United States Patent [19]

Wagner

[11] 4,344,191
[45] Aug. 17, 1982

[54] CHIN IMPLANT

[76] Inventor: Kurt J. Wagner, 14050 Valley Vista Blvd., Sherman Oaks, Calif. 91423

[21] Appl. No.: 225,216

[22] Filed: Jan. 15, 1981

[51] Int. Cl.³ .............................................. A61F 1/24
[52] U.S. Cl. ..................................... 3/1.9; 128/92 C
[58] Field of Search ................. 3/1.9, 1.91; 128/92 C

[56] References Cited

U.S. PATENT DOCUMENTS 3,720,959  3/1973  Hahn ..................................... 3/1.91
3,849,805  11/1974  Leake et al. ................... 128/92 C X

FOREIGN PATENT DOCUMENTS 2806207  8/1979  Fed. Rep. of Germany ........... 3/1.9

Primary Examiner—Clifford D. Crowder
Attorney, Agent, or Firm—Warren T. Jessup

[57] ABSTRACT

A chin implant molded of biologically inert material is surgically inserted and positioned on the outer surface of the mandible to form a build-up of the jaw. The surgical procedure is called a menoplasty. The implant is designed to give a natural contour to the shape of the jaw for patients who have receding chins. The implant has two notches on its upper edge which are adjacent to the mental foramens. The notches allow for physical clearance between the mental nerves and the implant.

5 Claims, 4 Drawing Figures

CHIN IMPLANT

BACKGROUND OF THE INVENTION

Plastic surgery has recently been developed to improve the cosmetic appearance of patients who, because of accident or genetic deformity, have various physical imperfections. A common condition known as hypogenesis, or receding chin, has been successfully dealt with by means of a chin implant surgically placed on the exterior of the mandible. Prior designs for chin implants have been of the converging concavo-convex lens-like or watchglass shape. When in place, and after healing from the surgery, this type of implant has created an artificial chin contour. That is, it did not achieve its objective, which is to give the patient a handsome, naturally appearing chin profile.

SUMMARY OF THE INVENTION

An object of the present invention is to have a chin implant which gives the appearance of a natural chin contour after surgical implantation. Past implant designs avoided the mental nerves which exit through the mental foramen on the lateral sides of the mandible or lower jaw. The present invention also seeks to avoid this mental nerve, but in a novel and unique approach, compared to the past implant designs. The old watchglass shapes when surgically implanted resulted in an unnatural chin contour and moreover the implant tended to drift and move out of position while eating or talking. Over a period of time this flotation or drifting of the implant within the confines of the jaw area tended to contact the mental nerves which resulted in inflammation and severe pain of these nerves. The present invention which has a solid crescent shape and bilateral tails tends to keep the implant in a more stable configuration around the jaw. The extended surface area between the inside face of the implant which abuts the jaw tends to keep the implant from drifting. Furthermore, the bilateral notches which are removed from the upper edge of the implant avoid the mental foramen out of which the mental nerves emerge. The notches prevent contact and subsequent irritation, and the notches furthermore are not visible once the implant has been surgically implanted.

A further object of this invention is to use a silicone or plastic implant which will be biologically inert and non-reactive to avoid infection of the patient's body.

DETAILED DESCRIPTION OF THE PREFERRED EMBODIMENT

Figure 1:
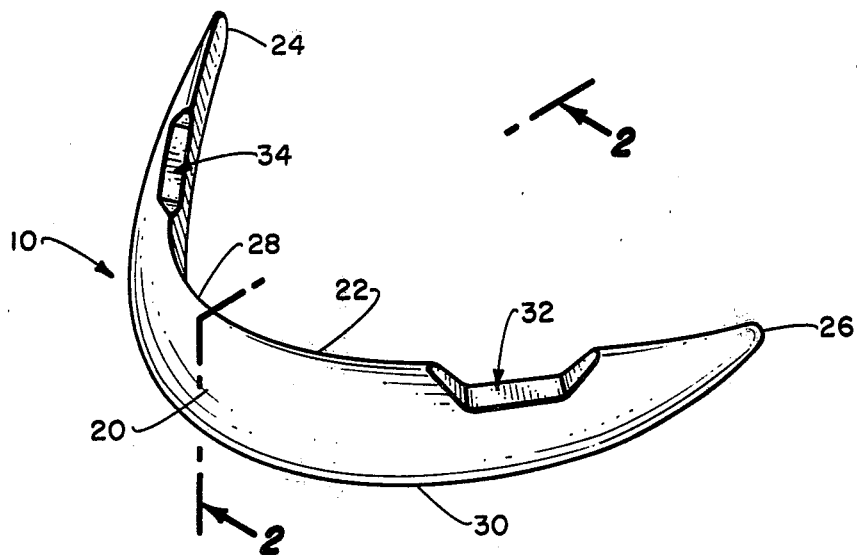
FIG. 1 illustrates a perspective view of the implant.
Figure 2:
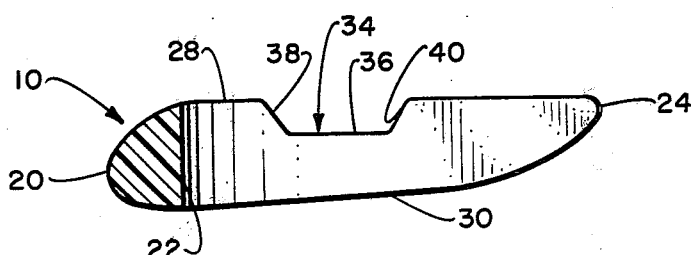
FIG. 2 is a cross-sectional view taken along the line 2—2 of FIG. 1.
Figure 3:
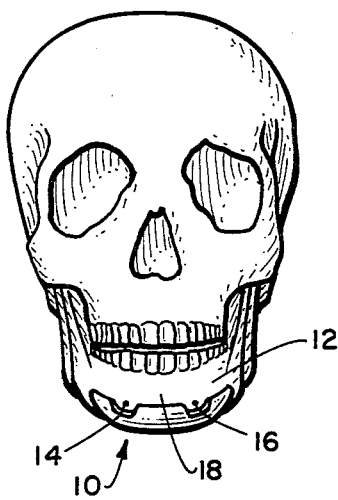
FIG. 3 is a frontal view of the human skull and mandible with the implant shown as correctly positioned.
Figure 4:
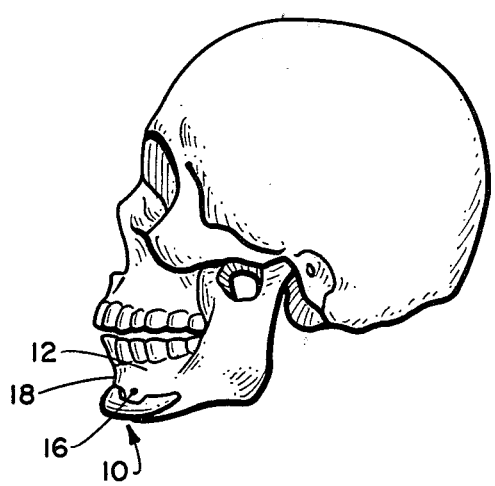
FIG. 4 is a profile view of the skull as depicted in FIG. 3.

A chin implant is illustrated in FIG. 1 and is generally designated by the numeral 10. In FIG. 3, the mandible is generally designated by the numeral 12. Also in FIG. 3, the bilateral holes 14 and 16 designate the mental foramens on the jaw or mandible. In FIG. 4, the leading edge of the jaw is generally designated by the numberal 18 and is called the mental protuberance.

Referring back to FIG. 1, the implant 10 forms a generally crescent-shaped solid configuration. The implant 10 has a front face 20 which is generally described as a curved convex profile. The back face of the implant 10 is generally described as a concave surface, designated as 22. The front face 20 and the back face 22 generally converge at the tail 24 and 26 on both ends of the implant 10. The front face and back face also converge with an upper edge 28 and a generally lower edge 30. The upper edge 28 contains two lateral notches 32 and 34 which can be integrated with the mold when the implant is fabricated. Alternatively, the notches 32 and 34 can be cut from the upper edge 28 for a custom fit on the particular surgical candidate. The notches 32 and 34 are hereinafter described in the singular sense by reference to notch 34 as if both are identical in configuration. Actually, notches 32 and 34 are mirror images of each other. The notch 34 contains a lower edge 36 and two outwardly slanting surfaces 38 and 40 which gradually slope towards the upper edge 28. The flat area 36 is of sufficient width and depth to avoid overlapping or covering the mental foramens 14 and 16. The notch 34 has a generally flat cut configuration; however, it is contemplated that the notch could be of a rounded smoothed-out configuration, if necessary. The notches are preferably specifically tailored to the requirements of the patient upon whom the implant shall be inserted. The notch 34 should be of sufficient width and depth to avoid the mental foramens in the average patient. Of course, the attending plastic surgeon may have to change the position of the notches because a patient may have the mental foramens in an unusual area. This can be determined through examination prior to the operation. It is foreseeable that the implant can be altered somewhat by filing, cutting or otherwise conforming the transplant to the mental protuberance against which the transplant will be positioned.

The back face 22 is designed to abut the surface of the mentum 18. The backside is generally of a flat, slightly curved concave configuration. The front face 20 is more sharply curved convex configuration. The difference in the curvatures of the front 20 and back face 22 results in a merger of both faces at each end 24 and 26. The tapering-off effect is adapted with the sides of a mandible. The tapering and thinning tails 24 and 26 will blend in with the mandible so that the implant 10, after being positioned into place, will add a natural contour to the patient's chin 12.

Obviously, many modifications and variations are possible in light of the above teachings. It is therefore to be understood that the full scope of the invention is not limited to the details disclosed herein and may be practiced otherwise than as specifically described.

What is claimed is:

1. A chin implant for cosmetic surgery in a human mandible which comprises:

a solid, crescent-shaped implant having a front face and a back face, each said face tapering bilaterally to form respective tails of the implant, and each face merging to form an upper edge and a lower edge;

said back face having a flat surface for placement adjacent to the mental protuberance of the mandible;

said front face having a curved projection surface for protruding from the chin to create a natural chin profile after implanting; and said upper edge having a pair of notches placed laterally thereon and adjacent to each mental foramen of said mandible for allowing a space between said implant and mental nerves.

2. The implant as recited in claim 1 wherein said front face includes a more sharply curved convex configuration, said back face includes a less sharply curved concave configuration.

3. The implant as recited in claim 1 wherein said front face has a generally parabolic transverse cross-sectional configuration midway between said tails.

4. The implant as recited in claim 1 wherein said implant is pliant, flexible and compressible.

5. The implant as recited in claim 1 wherein said implant is comprised of a plastic such as silicone.

* * * * *